United States Patent [19]
Cosman et al.

[11] Patent Number: 6,122,541
[45] Date of Patent: *Sep. 19, 2000

[54] HEAD BAND FOR FRAMELESS STEREOTACTIC REGISTRATION

[75] Inventors: Eric R. Cosman, Belmont; Robert A. Daniels, Haverhill; Michael A. Cundari, Hingham, all of Mass.

[73] Assignee: Radionics, Inc., Burlington, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/763,557

[22] Filed: Dec. 10, 1996

Related U.S. Application Data

[63] Continuation of application No. 08/435,515, May 4, 1995, abandoned.

[51] Int. Cl.[7] .................................................. A61B 5/00
[52] U.S. Cl. ........................ 600/426; 600/429; 606/130
[58] Field of Search .................................. 378/163, 205, 378/206, 164; 356/247, 248; 606/130; 128/653.1, 654; 600/40, 42, 414, 417, 426, 427, 429

[56] References Cited

U.S. PATENT DOCUMENTS 5,368,030  11/1994  Zinreich et al. ..................... 128/653.1
5,383,454   1/1995  Bucholz ............................... 128/653.1

FOREIGN PATENT DOCUMENTS

WO 94/23647  10/1994  WIPO ................................. 128/653.1

*Primary Examiner*—Ruth S. Smith
*Attorney, Agent, or Firm*—Darby & Darby P.C.

[57] ABSTRACT

A skin-based band is fixed to a patient's skin in a repeatable position and includes reference markers which, attached to the skin band, can be visualized in tomographic image scanning. The reference markers appear as reference marker images in the image scan data from the image scan and correspond to coordinate positions in the image scan coordinate system. The reference markers also provide corresponding reference marker positions in the physical space of the patient's anatomy, which may correspond to a stereotactic coordinate system associated with a digitized navigator or frameless stereotactic reference system near the patient. The band can also be placed on the patient again at the time of surgical intervention, and the reference markers can be touched or referenced by the surgical navigator in the stereotactic coordinate system. A computer system assimilates the image scan data and calibration data and enables a mapping from the image scan coordinate system to the stereotactic coordinate system so that surgical instruments can be tracked by a surgical navigator so that their position can be referenced to the image scan data.

6 Claims, 4 Drawing Sheets

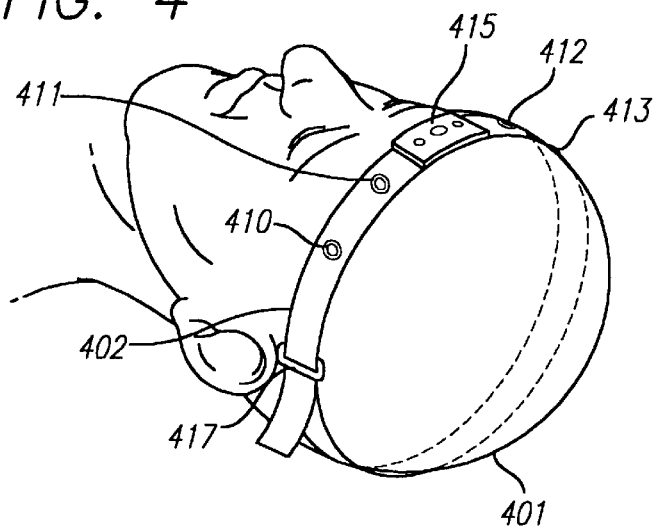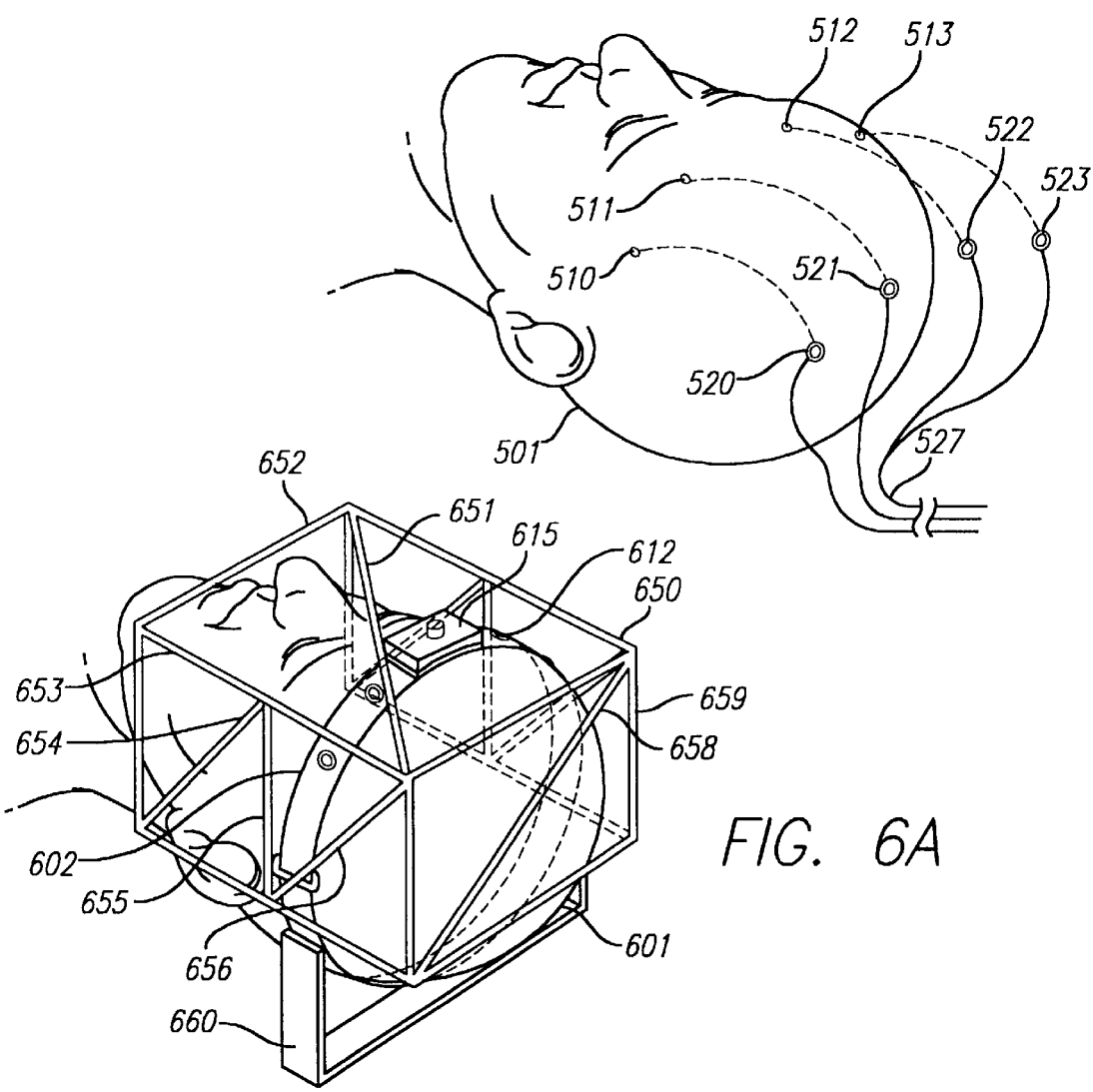

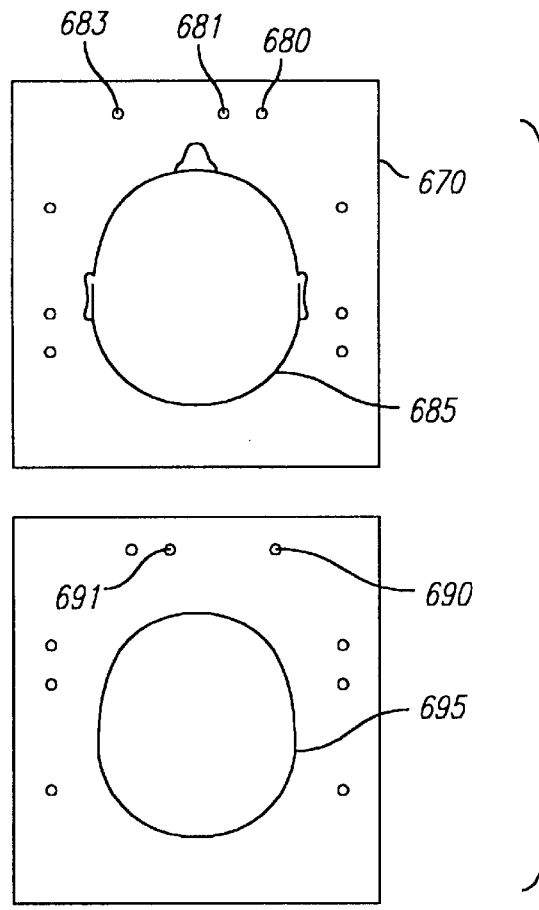
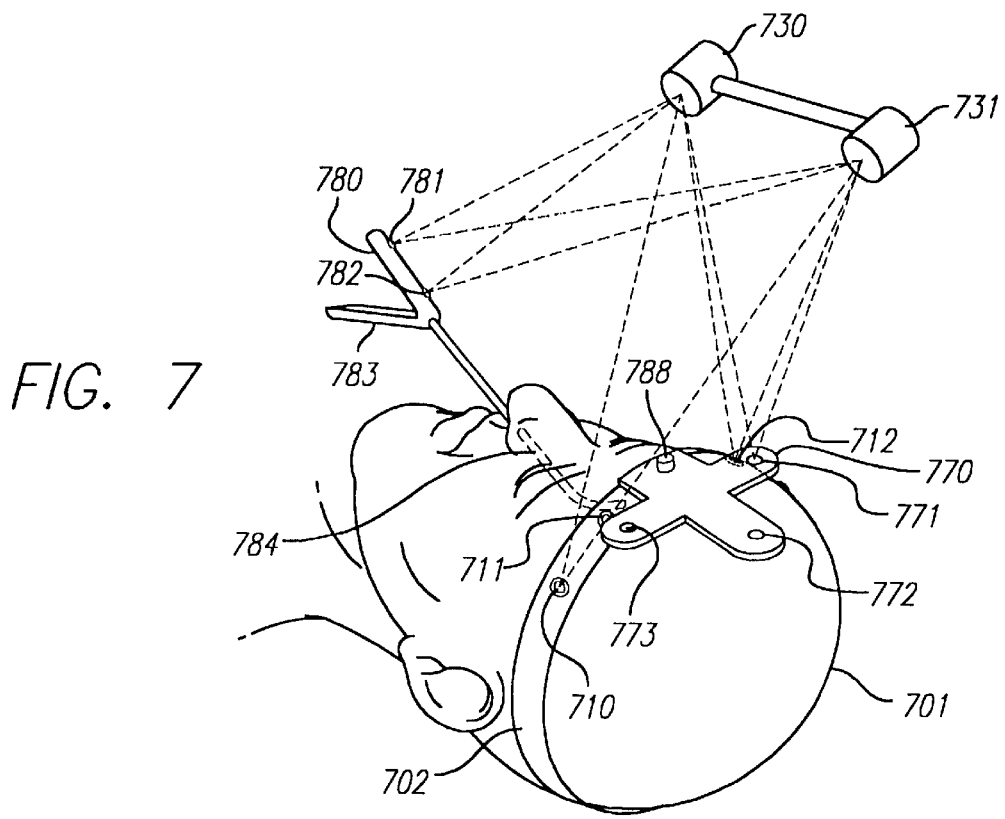
FIG. 6B
FIG. 7

HEAD BAND FOR FRAMELESS STEREOTACTIC REGISTRATION

This application is a continuation of application Ser. No. 08/435,515 filed on May 4, 1995 now abandoned.

BACKGROUND AND SUMMARY OF THE INVENTION

The field of frameless stereotaxy is now a very active one. In the early works of Watanabe (1986) and Kosugi (1987), and other workers such as Guthrie and Adler in the same time frame, a digitized space pointer or stereotactic navigator was used which involved an encoded mechanical arm. This navigating arm was placed near the patient during surgery. Typically, reference points such as radiopaque skin markers or tattoos where radiopaque skin markers could be placed were located on the patient's skin. The skin markers were in place at the time the patient is scanned by an image scanner prior to surgery, and they appeared as reference marker images on the image scan data from for example a tomographic scan. The scan could be from CT, MRI, PET, or other modality, and appropriate markers visible on these scans could be used. One of the objectives was to transform from the image scan coordinate system to a reference frame associated with the stereotactic navigator, and in the case of Watanabe, Kosugi, Guthrie, and Adler, this was the reference frame of a digitized mechanical arm. Other types of reference frames and associated digitizers have been developed involving ultrasonic, optical, and magnetic coupling between a probe whose position is to be determined or tracked in space relative to the patient and a detector or sender system which represents the reference system for the space digitizer located near the patient's head. At the time of surgery, such a probe, whose position can be determined in the digitizer coordinate system, (herein referred to as the stereotactic coordinate system) could be used to touch each of the reference markers in sequence, thereby determining their positions relative to the stereotactic coordinate system of the digitizer. At this point, since the positions of the reference points are known with respect to their reference point images in the image scan coordinate system, and the physical reference points positions are known with respect to the coordinate system of the digitizer or the reference (stereotactic) coordinate system in space, then a mapping, transformation, or correspondence can be made between these two coordinate systems. Thereafter, the position of the surgical instrument which is being tracked by the digitizer system can be represented in the coordinate space of the image scan data. Thus, as the pointer or surgical instrument is moved in space near the patient's anatomy, a representation of where it will be relative to the inside of the patient's head, as represented by the image scan data, can be determined. All of this data: the image scan data, reference marker images, digitizing data from the reference frame of the digitizer, positions of the physical reference markers, can be loaded into a computer or computer graphic workstation and the transformations can be made by matrix transformations within the workstation, as explained in Kosugi's paper. Thereafter the position of the space probe can be represented in the image scan data as a representation of the slice containing the tip of the probe, or slice containing the probe itself (as in an oblique slice) or representation of the probe within the 3-D slices, or 3-D rendering of the image scan data itself.

It would be convenient to be able to put the reference markers on the patient's body or head in a repeatable way and in a simple way for an operator. It would also be convenient to have a structure which can retain the reference markers so that they can be returned onto the patient's body repeatedly, as for example in the scan episode and in the surgical episode, so easy referencing of multiple markers can be done. It is also convenient if dynamic reference markers could be installed or coupled on the patient's body in a common structure with the reference markers, or convenient if the dynamic markers are the reference markers themselves which can be tracked by the space digitizer or its detection system in the coordinate reference frame of the space digitizer, so that the patient's movement can be tracked dynamically, and thereby corrections in the transformation between the image scan data coordinate system and the stereotactic coordinate system can be made. It would furthermore be convenient if the attachment means for the reference markers and the dynamic reference markers could also alternatively couple to a graphics reference means which can index all of the scan slices in a unified image scan coordinate system to eliminate errors due to patient's movement during the scanning or to correct for aberrations in the scan slice sequence itself.

Thus, it is an objective of the present invention to provide an apparatus, a means, and associated technique, which can easily attach to and which may be repeatedly re-attached to the patient's anatomy if desired, in essentially the same location which contains a plurality or pattern of reference markers to be used for frameless stereotaxy.

It is also an objective of the present invention that the patient attachment means can be placed on or connected to the patient's skin easily and that it can be quickly placed and re-placed at the time of scanning with minimal effort or technical knowledge.

It is also an object of the present invention that the patient attachment device can include dynamic reference markers which can be detected rapidly by the space digitizer or the space digitizer detection or transmission means so that rapid corrections of patient movement, either in the scanner or in the operative setting, can be made so as to correct the transformation between the image scan coordinate system and the stereotactic coordinate system of the space digitizer.

It is an objective of the present invention to provide a system which is non-invasive and would not necessarily require breaking of the patient's skin or any discomfort for the patient to have the patient attachment device installed on the patient.

It is also an object of the present invention to provide a patient attachment device which can be cooperatively coupled to a graphic reference means with diagonal and parallel elements such that the image scan slice data or tomographic scan data can be indexed relative to the patient attachment device, and therefore to the patient's body, in a consistent image coordinate system.

DESCRIPTION OF THE FIGURES

FIG. 4 shows an embodiment of the present invention which is a head band strapped around the patient's head with reference markers in place and a docking structure attached to it.

FIG. 5 shows ink marker tattoos on the patient's skin which enable a head band to be repositioned on the patient's head repeatedly, or individual LED markers to be placed on the tattoo positions.

FIG. 6A shows a graphic reference structure with parallel and diagonal elements that is coupled to the head band to provide image scan data as in FIG. 6B with varying index data so as to index the tomographic slices relative to the reference markers and the head band and/or for indexing of the image scan data with respect to the physical reference markers and/or the graphic reference structure.

FIG. 7 shows the head band with dynamic reference markers installed on it; in this embodiment, the dynamic reference markers are LED lights which are detected by an optical tracking system, and in the same figure an ENT probe which is used for nasal surgery with optical tracking.

DESCRIPTION OF THE INVENTION

The embodiments below are meant as illustrations of the invention, and not to limit the scope of the invention. Those skilled in the art can think of other embodiments and variations which fall within the scope of the present claims.

Figure 1:
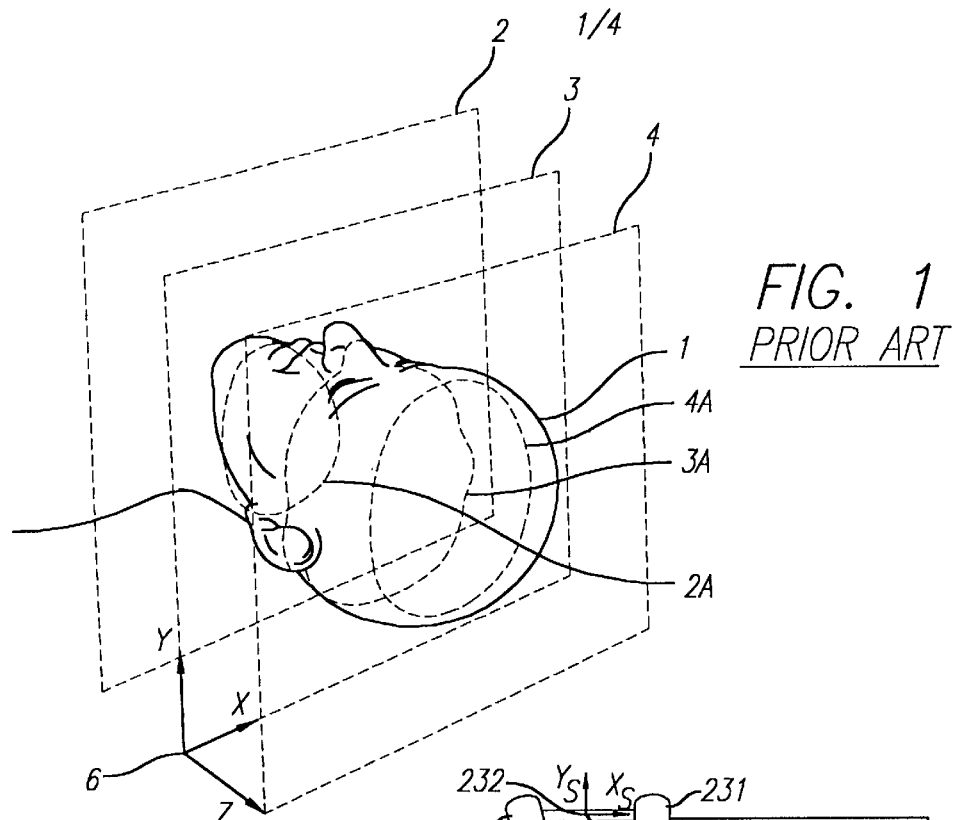
FIG. 1 shows a typical tomographic imaging machine coordinate system with schematic slices through a patient's anatomy.

Referring to FIG. 1, the patient's anatomy 1, which in this case is his head and neck, is being scanned by tomographic slices illustrated by slices 2, 3, 4, and there could be many more slices in a typical scan sequence. These slices typically are taken from a CT scanner with X-rays or an MRI scanner, PET scanner, or other modalities. Although they are shown as slices, such scan data can be taken volumetrically or with a spiral scanner in modern scanners. The image scan data from the image scanning machine, such as a CT tomographic machine, usually can be referenced to its own coordinate system, the image scan coordinate system. In FIG. 1, this is illustrated by the X, Y, Z coordinate system 6 which has the X and Y axes related to the orthogonal axes of the two-dimensional scan slice, and the Z axis representing the scan number, scan depth, or scan position in space relative to the scanning machine, and this is typically orthogonal to the scan slice plane. Thus the image scan data can be referenced, in this example, relative to the three-dimensional coordinate system 6. The scan data usually is processed through an image scan computer and then can be sent to an off-line computer graphic workstation which can be used in conjunction with a stereotactic navigator or stereotactic space probe or digitizer. The data can be rendered in three dimensions or it can be left as two-dimensional slice data, and the position of the space probe can be indicated within that slice data or three-dimensional representation. Examples of this are given in the papers by Watanabe, et al and Kosugi, et al referenced above. As seen in FIG. 1, the intersection of each of the slices 2, 3, and 4 with the external anatomy or the skin of the patient are represented by the contour lines 2A, 3A, and 4A respectively. In each of these slices, the patient's internal anatomy is represented. What has been described so far is prior art, and known in the image scan technology.

Figure 2:
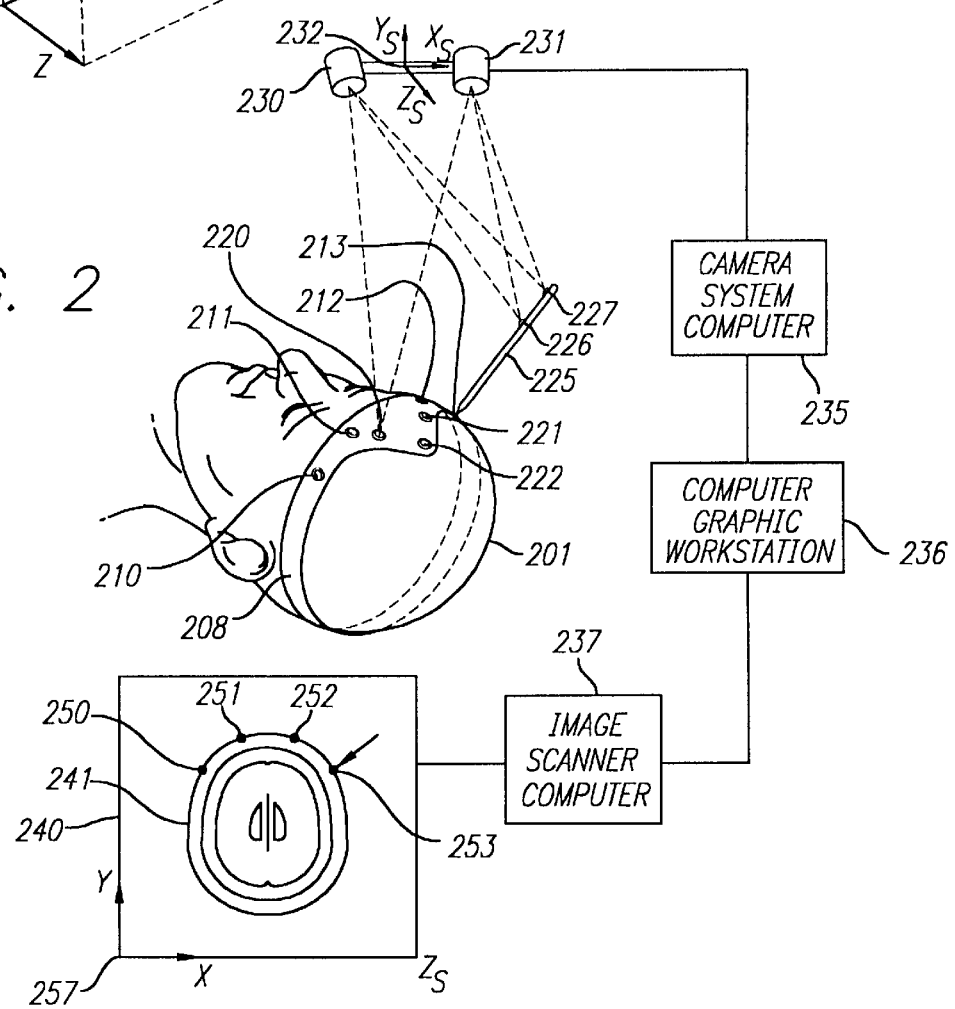
FIG. 2 shows an embodiment of the present invention involving a head band strapped around the patient's head with reference markers and dynamic reference markers in place and an optical digitizing system with the probe referencing to image scan data.

FIG. 2 shows an embodiment of the present invention, which in this case is a skin band or head band 208, which is secured around the patient's anatomy, in this case the patient's head 201. This band could have been illustrated as being a stick-on, flexible plate, or other type structure which can be attached to the patient's skin, and the skin could be located on any part or any portion of the patient's anatomy throughout the body. In this example, reference markers 210, 211, 212, and 213 are positioned in some fixed relationship to the head band, and thus as the band is secured to the patient's head, the reference markers are essentially in a fixed relationship to the patient's head. These reference markers can be radiopaque dots, radiopaque rings, or other structures which are visible in an X-ray, CT, tomographic scan, or they may be MRI visible, or PET visible, or of other construction to be visible in other scanning modalities. As an example of a digitized navigator or space probe which can be used in a frameless stereotactic context, FIG. 2 shows two cameras 230 and 231 which are mounted on a bar between them and fixed in the operating theater on some external apparatus. The camera system has an associated stereotactic coordinate system 232, which is represented by the axes $X_s$, $Y_s$, and $Z_s$. The cameras in this case may be two two-dimensional cameras viewing the field near the patient. In the field is a surgical probe, or surgical instrument, or surgical apparatus, or other external apparatus, as the case may be, which is represented generically by the element 225. It has optically detectable elements 226 and 227 on it, which might represent two light-emitting diodes (LEDs) which are visible and can be tracked in position by the cameras 230 and 231. In this way, the position and orientation of the probe relative to the cameras can be determined, and that data can be assimilated in a processing element (designated as a camera system computer 235), which might be circuitry and a computer associated with it which can read out data from the camera system. This data, for example, might be the coordinate position data of the instrument 225 relative to the camera coordinate system, also referred to here as the stereotactic coordinate system. In a typical procedure (but not the only procedure for frameless stereotactic registration.) the point of the space probe or digital navigator might be touched to one of the reference markers 213, and thereby the coordinates of the reference marker with respect to the stereotactic coordinate system can be determined. The position of the other reference markers may also be determined in the same way. Thereby, the position of the reference markers and/or the reference structure attached to or associated with the head band can be determined with respect to the stereotactic coordinate system or the camera coordinate system. Similarly in FIG. 2, there is shown an image scan or image slice 240, which in this case happens to have reference marker images 250, 251, 252, and 253 corresponding to the reference markers 210, 211, 212, and 213 in the physical space of the patient. Each of these reference marker images may have coordinates in the image scan coordinate system 6 of FIG. 1. This coordinate system with respect to the scan 240 might be indicated by the coordinate axes 257, which are the orthogonal axes within the scan slice; and in addition, there is a Z coordinate which might be the slice number indexed by the appropriate slice spacing. By making a mapping, transformation, or other referencing of the coordinate data associated with the reference markers in the stereotactic coordinate space to the reference marker images in the image coordinate space, a transformation or mapping between the image scan coordinate system and the stereotactic coordinate system can be made. Such a transformation is described in the article of Kosugi, et al. It might also be added that schematically in FIG. 2 is shown the element 237 (designated as an image scanner computer), which might be the image scanner or the computer associated with the image scanner or a means for handling computationally the image scan data and the coordinates of the reference markers. This image scan data may be fed to the element 236 (designated as a computer graphic workstation), which may be a transformation means or maybe a computer graphic workstation or other computer means. Element 236 can process the data from the camera system 235 and the image scan data, and perform the transformations computer discussed above. Once these transformations are in hand, then the position of the probe 225 in real space can be mapped to its virtual position in the image space or scanner coordinate system of the image scan data. Thus, on a computer graphic display means such as a CRT screen associated with the computer graphic workstation 236, a position of the space probe can be displayed relative to the image scan data. The tip of the probe can be made to correspond to one or more image scan slice(s), the orientation of the probe can be shown in projection or in three-dimensional space relative to the image scan data, etc. These are standard manipulations now known in frameless stereotaxy.

Also indicated in FIG. 2 as part of the head band are ancillary or additional reference markers indicated by the numbers 220, 221, and 222. They may be light-emitting diodes or other optically reflecting or optically visible objects which are in a fixed position or affixed to in a predetermined or non-predetermined position onto the head band 208, and are detected by the cameras 230 and 231 so that their position can be determined in the stereotactic coordinate space. These ancillary or dynamic reference markers may be in a pattern such that their orientation can be determined and therefore can be a representation of the position or movement of the patient's head with the head band in place. Such a movement of the patient's head will give rise to a change in the coordinate transformation between the image scan coordinate system, which is taken relative to the patient's head, and the stereotactic coordinate system of, in this case, the cameras, which may be fixed relative to the room or operating couch where the operation takes places. Thus, a modification of the transformation would be needed, and this can be corrected for by knowing the changes in the orientation of the dynamic reference markers. For example, in FIG. 2 there are three dynamic reference markers, and their positions can be detected in space by the cameras. If the patient's head moves, then a coordinate system which is affixed to the patient and therefore in a rigid body orientation relative to the head band, such as the dynamic reference markers, will also move. The movement of the patient's anatomy, in terms of a translation and rotation movement, can be taken into account by the movement in terms of translation and rotation of the head band dynamic reference markers. In this way, the camera system or navigator system can be continuously monitoring the position of the dynamic reference markers on the patient attachment device, in this case the head band, and a correction can be made to the coordinate transformation to take into account this rearrangement of the patient's head. Additionally, the cameras or other digitizer can be coupled to the patient's head by use of a fixation device. Indeed, any relative movement of the camera system and the patient's head can be so taken into account by the cameras monitoring these dynamic reference markers. The dynamic reference markers themselves could in fact be part of the reference markers on the head band shown in FIG. 2; that is to say, elements 210, 211, 212, and 213 themselves may be dynamic reference markers and can be identified or detected by the camera system for that purpose. On the other hand, the dynamic reference markers may be separable or distinct from the reference markers, as is illustrated in FIG. 2, and they can serve the separate functions described above or a unified function. The dynamic reference markers may have a predetermined pattern and can be affixed in a predetermined way to the head band so that their relationship with the reference markers may be know or predetermined. Alternatively, it is not necessary that they be in a predetermined relationship to the reference markers, since the correction to the coordinate transformation may be done without such a predetermined relationship. The dynamic reference markers, and indeed the reference markers, may have LEDs connected to them so that they become optically coupled to the camera system. They may be corner cube reflectors or other types of reflecting or light-gathering devices, or simply their pattern can be identified by the cameras so that their position can be determined and tracked, as described in the dynamic transformation correction.

Figure 3:
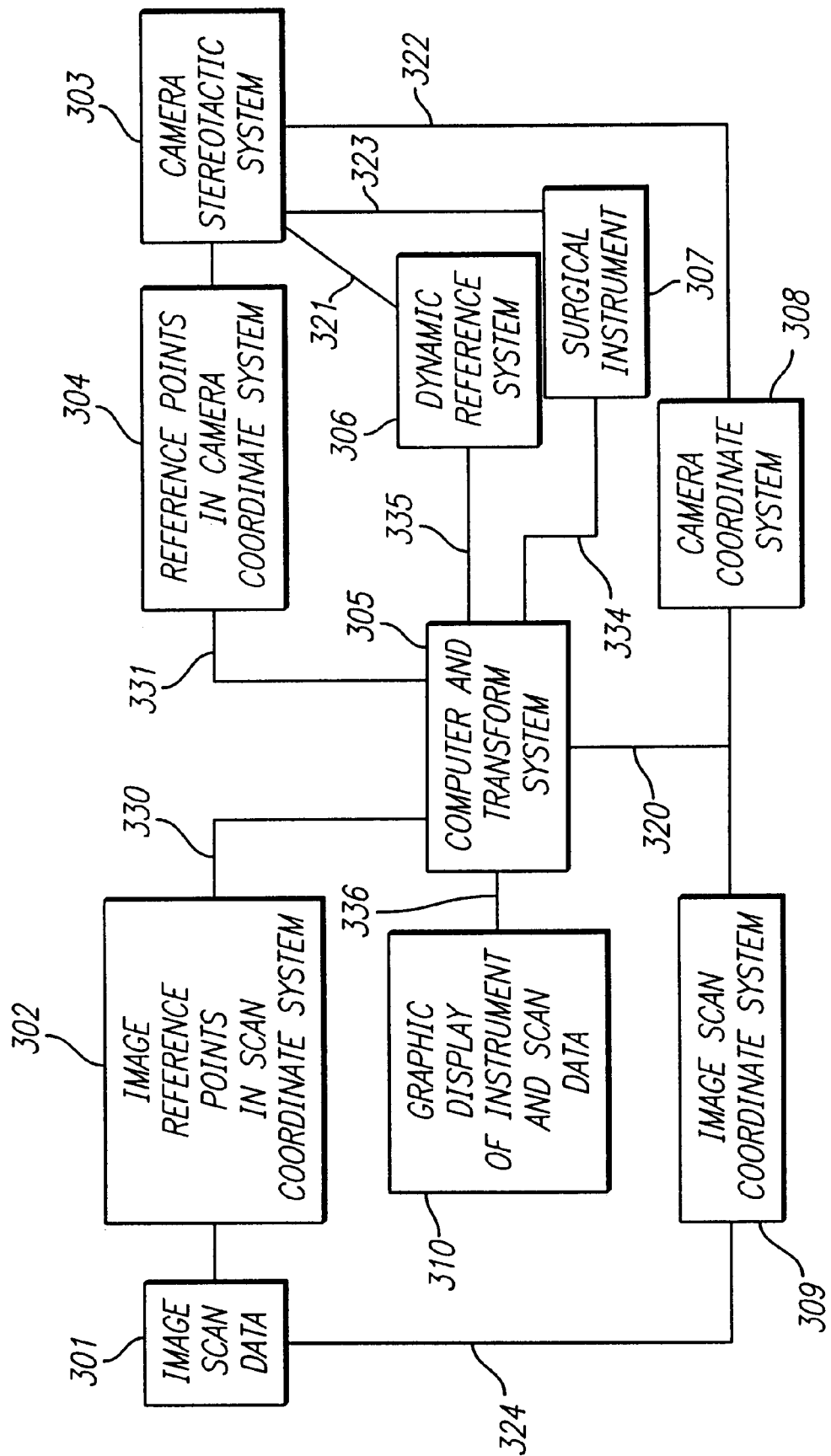
FIG. 3 shows a schematic block diagram representing one example of how image scan data and physical data from the space navigator can be transformed from one to the other so as to transform the image scan coordinate system to the stereotactic coordinate system of the space digitizer and displays of probes and surgical instrument movement in the surgical field can be represented on image scan data via a computer graphic workstation.

FIG. 3 shows one schematic example of the elements or steps in the process of using the skin band with dynamic reference markers and reference markers. Element 301 represents the image scan data plus the scan machine, and this gives rise to element 302, which are the images of the reference points or reference markers within the scan coordinate system as identified in the image scan data. This information can be determined automatically or by manual pick-off and be fed via line 330 into a computer 305, which may be part of the image scan computer or may be an off-line computer workstation, as the case may be. The image scan data has associated with it (as represented by line 324) an image scan coordinate system represented by the element 309, and this has been described in one embodiment as part of FIG. 1. The external reference system or stereotactic system can be represented by element 303, and in the example of FIG. 2, it is a camera system. Many other types of reference system or technique could be imagined, for example, a mechanical coupling system, ultrasonic coupling, electromagnetic coupling, radio frequency coupling, or other means so as to determine the position of physical objects in space in the stereotactic coordinate system. The coordinates of the reference points can be determined, as illustrated by the element 304, and an example is given associated with FIG. 2. This information about the coordinates of the reference points relative to the stereotactic coordinate system can be fed, as by line 331, into the same computer system 305 as the image scan data. Thereby, a transformation action (represented for illustration purposes as line 320) can be made between the image scan coordinate system 309 and the stereotactic coordinate system 308, illustrated here as the camera coordinate system. The camera coordinate system can be a coordinate system associated (as represented by line 322) with the structure holding the cameras or with one or more of the cameras which are observing the surgical field. One (position-sensitive) camera, two cameras, or a plurality of cameras can be used equivalently and can be implemented for the purpose described above.

The dynamic reference system is illustrated by the element 306, and it is coupled (as represented by line 321), in the case of FIG. 2 optically coupled, to the stereotactic coordinate system. For example, the dynamic reference system may be tracked by the camera system in position and orientation. The position of the dynamic reference frame may be sent (as represented by line 335) to the same computer 305 as is the camera data, reference data, and image scan data. Thus, a correction to the transformation 320 involving, for example, a translation and rotation correction can be made to the coordinate transformation 320. In addition, surgical instruments or apparatus such as surgical tools, cutters, suction tubes, aspirators, bipolar forceps, endoscopes, etc. can be represented by the element 307. Element 307 could also include multiple instruments or instruments plus other surgical devices such as a microscope which is instrumented with lights and LEDs to be tracked (as represented by line 323) by the camera system. These all can feed (as represented by line 334) their own position data into the same computer workstation -305, and the entire scene can be tracked by the computer so that one has an integrated view of the instruments, the microscope, the dynamic reference points, etc. This may be provided by the graphic display 310 which may be connected to the computer 305 via line 336. All of them can be set in the same coordinate reference frame as the camera system, and their relative positions can be determined so that the microscope, for example, can point in a direction which is determined relative to the image scan data. The surgical probe can also be determined relative to the image scan data, all of it corrected by the dynamic reference markers on the head band.

Referring to FIG. 4, an embodiment of the present invention is shown which includes a head band 402 which is secured around the periphery of the patient's head 401 as in a conventional head band. It has a strap 417, which could be a Velcro strap or other tightening element so as to secure it with comfortable pressure around the patient's head. On the head band are reference markers 410, 411, 412, and 413. Any number of reference markers can be used, but it is convenient to have three or more so that one can more accurately reference the image slices as they pass through the reference markers. If there are three reference markers that are substantially non-colinear, then these reference markers can determine effectively a plane. Therefore such a pattern of reference markers can define the coordinate system of the image scan data coordinate system which can then be mapped to the coordinate system of the patient's anatomy or to the stereotactic coordinate system of the external reference apparatus associated with the stereotactic device or space digitizer. In FIG. 4, the reference markers such as 410 are annuli or rings which may be radiopaque or MRI visible or PET visible. They may have holes through them which enable visualization of the skin below, and indeed an ink mark can be made on the skin through each hole so as to reference where the head band was placed on the patient's head. For example, the head band could be put on the patient's head at the time of scanning and permanent or non-permanent ink marks can be put on the patient's forehead or scalp through these holes at the time the head band is put on. Then, at the time of surgery or repeat scanning or intervention, the head band could be replaced on the patient's head in substantially the same position by lining up the holes in the reference markers to the ink marks which are already on the patient's head, and then the head band can be secured in place by the straps or other means. In this way, a repeat reference frame is possible with such a head band. Other means of repositioning the head band are also possible such as lines, index spots, notches, or other means so as to reference it on the skin by means of ink markers or even anatomical or natural landmarks such as positions on the brow, over the ear, etc. Also shown in FIG. 4 is a docking platform 415. This can take many forms, means, and designs, but in this case it is a plate with, for example, index pin holes and a threaded hole to secure other devices to the head band such as dynamic reference markers or graphic reference structures to be described below.

FIG. 5 shows the same patient's head with reference markers or ink markers 510, 511, 512, and 513, which may correspond to the positions of the reference markers or hole positions 410, 411, 412, and 413 in FIG. 4. Such ink dots can then be used to secure either radiopaque reference markers later, or perhaps to secure a string of LED or optically effective objects which can be placed on the patient's head in essentially the same position as the reference markers of FIG. 4. These optically detected markers can then act as reference markers for a camera system which is viewing or monitoring the patient's anatomy, and thus the patient's anatomy can be tracked by these points such as 510, 511, 512, and 513 continuously during the time of intervention or surgery. For example, as shown in FIG. 5, a string of LEDs 520, 521, 522, and 523, with a common cable 527, can be in a bundle, and each of these stuck down over each spot, such as 510, 511, 512, and 513, at the time of surgery, as indicated by the dashed lines, and the patient can immediately be mapped into the image scan coordinate system by the transformation referred to in association with FIG. 3. The cameras could be tracking the position of the LEDs in their position on the patient's skin continuously, and the movement of the patient can be corrected for by a correction in the transformation of mapping described above. Thus, these spots such as 510, 511, 512, 513, etc. can act as mapping elements or reference markers themselves; they can be radiopaque or MR compatible buttons, or dots, or rings, or other objects stuck onto the patient's skin directly, corresponding to the position of the head band markers; or they can be optically detectable reference points, for example LED's or light reflectors, or skin attachment points that can be tracked by, for example, a stereotactic camera system or stereoscopic cameras so as to reference the patient in the coordinate system of the camera system and/or track the patient's position dynamically during a surgery with respect to the camera system or with respect to other apparatus in the room such as a microscope whose position is known relative to the external coordinate system.

FIG. 6A shows another embodiment of the present invention which involves a graphic reference means or graphic reference structure that is attached to the head band or skin band so as to index the tomographic slice data as it is taken. In this instance, a frame structure is attached by the docking mechanism 615 in a known, or a prescribed, or predetermined position relative to the head band 602. On the head band are shown also, for example, the reference markers 612, etc., which have been discussed previously. The graphic reference frame is rigidly or fixedly attached, and comprises vertical rod elements such as 650 and 653 together with diagonal elements such as 651, 654, 656, and 658, and there are others on the opposite side shown in dashed lines (not numbered), and there could be many more around the structure. In reference to FIG. 6A, the terms-"vertical" and "horizontal" are defined relative to a view of the patient when the patient is in an upright position, not when the patient is in the supine position depicted in FIG. 6A. In addition, there are horizontal rods 652, 655, etc. (and others not numbered) for example, and others on the top as well as horizontal rods running from anterior to posterior relative to the anatomy such as 659, all of which can give rise to index markings when a tomographic slice passes through the anatomy and the graphic reference structure. Tomographic slices can be axial, sagittal, coronal, or oblique, and they will give rise to two-dimensional tomographic images such as that shown in FIG. 6B. In FIG. 6B, one sees two representative schematic image slices. The top slice 670 shows the patient's anatomy 685 and fiducial index marks such as 680, 681, and 683, which might correspond to the CT image slice intersection of the rods 650, 651, and 653, respectively, on the graphic reference means of FIG. 6A. In the lower figure in FIG. 6B, another slice is shown, and one can see that the relative positions of the index marks 690 and 691 that correspond to rods 650 and 651 differ from the positions of marks 680 and 681. Such variation of image scan data can be used as a direct indexing, or mapping, or confirmation of the position of the scan slice. This is known from the work of Brown and the Radionics BRW and CRW Stereotactic Systems, in which case such a graphic reference means is used in conjunction with a stereotactic head ring for stereotactic indexing of tomographic slices. Other graphic reference structures or means could be devised by those skilled in the art and could be attached to the head band or skin band of the present invention. For example, the number of diagonals and rods could vary greatly. In fact, there could be only one vertical rod such as 650, and significant information on the indexing of the slice or the variation of head movement could be gained from that, such as head movement in the image scanner, etc. One of the advantages of such a graphic reference means attached to the patient is that if the patient moves from one slice to the next, then the index mark such as those shown in FIG. 6B can indicate the movement, and it is possible when assimilating the image scan data in a computer workstation to make corrections for this so that it can be placed in a consistent image scan coordinate system referenced, for example, to the patient's anatomy, or the head band, or the graphic reference means. For example, the image scan data can be referenced to a coordinate reference frame attached to the graphic reference structure, and all data from the image scanner can be transformed into that coordinate reference frame. The computer graphic workstation described in FIG. 3 can assimilate that image scan data, and it can be transformed directly from the coordinate system associated with the graphic reference means, as in FIG. 6A, rather than the coordinate system of the image scan machine as described in FIG. 1. Thus, this is an alternate possible mapping of the image scan data to the camera coordinate system. Should the patient move between slices or during the scanning or from one scanning episode to another, then the registration of any given slice or temporal collection of data can be referenced to this one common, patient-based or graphic-reference-structure-based coordinate system, and all of the data, therefore, can be in a consistent, unified data set. This data set can then be transformed to the stereotactic coordinate system of the camera or space navigator, and thereby errors can be corrected for and/or avoided. Another element which can help in this direction is a patient stabilizer such as that shown schematically as 660 in FIG. 6A. This may be a head clamp, or a head securing element, or an element that can be attached to the image scanner table, to the operating table, or to a treatment table such as for a LINAC in radiation therapy or stereotactic radiation delivery that can be secured to the head band 602, and thereby stabilize the position of the patient's head against movement. It can be a very secure or less secure clamp, and it can help the patient himself, if he is a cooperative patient, to resist movement during the scanning or during the operation. Thus the present invention comprises patient securing or fixation elements which can be attached to the skin band or head band. Such securing elements can be in turn fixed to the CT scanner couch or table or to any other couch or table associated with surgical intervention or radiation delivery. The graphic reference structure or means of FIG. 6A may include only one diagonal element, or one diagonal in conjugation with one parallel element, or a multiplicity of other elements whose geometry can enable referencing of the image scan data to the patient's anatomy so that movements in the patient's anatomy can be corrected for or taken into account. For instance, it may include a sequence, series, or pattern of radiopaque or MRI-visible dots, lines, rings, etc. so as to reference or index the image scan data. Furthermore, the data, when collected with such a graphic reference means, can correct for any aberrations in the scanning process itself. As is used in stereotaxy with stereotactic head frames, data can be collected and questions of alignment of the scanner to a base plane such as the head band or the base rod elements of the graphic reference means can be checked or confirmed, and full mathematical transformations of data can be made, if necessary, from images of the graphic reference means or structure to the base frame, in this case the head band or the element secured to the patient's body or skin.

FIG. 7 shows a further embodiment of the present invention in which dynamic reference markers are attached as an independent element to the head band. The head band 702 is again secured around the patient's head, and it has the reference markers 710, 711, and 712, as described above (other markers could be present). In addition, there is the dynamic reference structure 770, which can be secured to the head band by a securing element 788, and this may be secured to the patient before, during, or after scanning, or only during the surgical or interventive procedure. On the dynamic reference marker plate 770, there are the dynamic reference markers themselves 771, 772, and 773, which may be optically detectable structures or LED lights or other transmission or receiving elements for the spatial navigator reference system or external referencing apparatus, which in FIG. 7 is indicated by the optical cameras 730 and 731. These cameras are able to track the position of the dynamic reference markers, and thus track the orientation of the patient's head via the head band and correct for any head movement, as described above. Also shown in FIG. 7 is a surgical instrument 780, which has an offset handle 783 and LED or optically-detected index markers 781 and 782 which can be detected by the camera system 730 and 731. Thus, the orientation and position of the probe can be tracked in space, and, in particular, the position of the shaft of the probe 784 and its tip within the body can be tracked with respect to the camera system and therefore with respect to said patient's anatomy and with respect to the dynamic reference markers discussed above. The entire system can be an integrated system, where the relative positions of the probe and the patient's head can be tracked and differences can be determined. The reference markers 710, 711, etc., for example, on the head band could be used as dynamic reference markers as well, and the dynamic reference plate could be used as reference markers in the CT image scan also. Variations of this scheme can be devised by those skilled in the art. For example, the number of dynamic reference markers or reference markers can vary greatly, and their location and configuration can also vary to suit the situation. Discrete reference markers do not need to be used, but rather linear marks, or grid patterns, or other shapes that can be recognized by the camera system can be used. Intelligent software or artificial intelligence can be invoked so as to recognize patterns such as the head band, or the dynamic reference plate, or the reference markers and thereby the orientation of the patient's head, and other aspects of the scene can be determined and tracked. Similar remarks can be made about the probe 780. It can have a pattern of optically trackable markers or a shape of an optically detectable structure such that its position, orientation, and rotation can be determined in space. The scene in FIG. 7 is a typical one in the case of ENT surgery. A second instrument could be used in the patient's other nostril for sinus surgery. For example, that other instrument could be an endoscope with light-emitting diodes on it so as to track its position. A multiplicity of cameras could be used, and even one position-sensitive camera can be used, if appropriately designed for range viewing to perform this function shown in FIG. 7. Typically, two or more cameras are useful to get a stereoscopic view or to have redundancy in the detection system, or to increase the range of angles of observation for a given surgical setting so as to eliminate line-of-sight problems. The dashed lines in FIG. 7 are meant schematically to illustrate the optical coupling between the cameras and the respective elements described here.

Many variations of the invention described here can be thought of by those skilled in the art. For example, the head band might be adapted to be placed around the patient's torso, his limb, or some other portion of the anatomy. The head band need not be an entire encirclement of the body, but could be taped on or stuck down to the body. For instance, it could be a bandage-like structure that could be stuck to the forehead and it could have adhesive on its lower side to provide a secure sticking to the patient's skin. It could be a Velcro strap with an elastic band around the back, or it could be something akin to a pair of glasses which hook over the ear. Such "glasses" otherwise could be secured by straps over the head and perhaps around the back of the head near the neck.

The skin band may take various forms and variations. It could be, in fact, a head band made of a thin plastic such as polyurethane, or polypropylene, or other thermal plastic; it could be a plate structure made out of plastic or other material such as carbon fiber or metal; it could be a strap such as a nylon strap or a Velcro strap; it could be something analogous to a surgical stick-on band-aid; it could be a stick-on band; it could be a head band or a cloth band that can wrap around the patient's head or the patient's anatomy and be bound to it by a strap, or clasp, or buckle system; it could have multiple bands, one going around the azimuthal circumferencial direction of the patient's head, for example, and another that goes over the top of the head in various directions such as sagittal, coronal, or other oblique paths; it could be similar multiple band structures wrapping around the patient's torso or the rest of his body, either in parallel bands or in random orientations; it could have attached to it or attachable to it a graphic reference device or graphic reference means which might be, for example, a hard hat, or a dome, or a helmet which has multiple, spatially-located reference markers that can be seen in the image scan and also located in the physical space. Also such variations are possible associated with the skin band. A very simple embodiment, as shown in the figures, is a simple belt which wraps around the patient's head or body that can be cinched and easily applied by a technician during scanning and re-applied in a replaceable or identical position at the time of surgery, such as for ENT surgery or even neurosurgical interventions. This would be a very convenient embodiment of the present invention. Such a belt-like structure or band-like structure could be disposable for essential single patient use. It could come sterile-packed or it could be autoclavable. For example, if it were made out of a high temperature thermoplastic, it could be easily molded and the reference markers or index hole positions could be molded into it so that each is exactly identical to another. The reference band could come in a kit form which includes a head band, an ink pen for skin marking, a dynamic reference marker system with LED lights and attachable cord, and a disposable graphic reference structure with diagonals or other points on it for the dynamic referencing of the patient's head. Such a kit could be disposable and intended for single patient use.

There can be wide variations in the placement and configuration of reference markers and dynamic reference markers, as described above. The skin band may be more akin to a pattern of reference markers on a sheet structure which can be secured or stuck to the patient's skin. The skin band may be similar to a string of reference markers or LED lights that can be stuck down on a position or positions, as for example the ink mark positions that might be represented in FIG. 5 on a patient's forehead or in other locations on his skin. The skin band, reference markers, and dynamic reference frame could be used in conjunction with external apparatus for tracking the relationship of the apparatus to the patient's head. For example, cameras could be mounted on a microscope or on a linear accelerator (LINAC) for external beam irradiation of the patient so that the relative orientation of the patient on the linear accelerator's couch, or near the microscope, or relative to the beam delivery system of a radiation system could be used for the purpose of aligning the patient or tracking the position of the patient as he is moved into position for surgery or external treatment. Any such variations of the use of a skin band, or skin-fixed reference markers, or skin-fixed light systems are intended to be included within the scope of the present invention.

A great variety and variation in the graphic reference means, as shown in the embodiment of FIG. 6, can be thought of and devised by those skilled in the art. The structure could be MRI and CT visible and thus be made of hollow tubes which can be water-filled. The structure can be made of diagonal plates or otherwise wire cage structures so as to provide the graphic reference means for the image scan data, as described above. The attachment to the skin fixation means might be done in a variety of ways other than the docking system described in FIG. 6. Such graphic reference means could be attached to the patient's torso or limbs so as to give local referencing to the anatomy within those parts of the body. The graphic reference means could be flexible or curvilinear in its structures and be attached in a molded fashion to the patient's body on or near the skin band structure, or it could be stuck down to the patient's body in conjugation with the skin band so as to achieve the kind of referencing of the image scan data as described above. All such variations are intended to be included within the scope of the present invention.

It should be noted that the graphic reference structure may have a coordinate system of its own, which we might refer to as a graphic reference structure coordinate system, and this can be transformed or mapped into the image scan coordinate system, or data which is referenced with respect to said graphic reference means coordinate system can be mapped into or back from the image scan coordinate system. In this way, corrections associated with movement or change of position of the patient's anatomy in said image scanner as the scanning is being done can be made, and therefore corrections of such variations due to patient movement, or even aberrations of the image scan coordinate system, or slice indexing, or, for example, scanner couch tilt can be corrected for. Thus, the image scan coordinate system can be transformed into a graphic reference structure coordinate system, and the graphic reference structure coordinate system can be used as the basic image coordinate system that is mapped to the stereotactic coordinate system of the space navigator. As another example, the image scan data can be referenced, as it is being taken, to the graphic reference structure coordinate system, and that coordinate system can be used as a reference coordinate system analogous to the image scan coordinate system but, in this case, reference to the graphic referenced structure, which is in turn referenced to the patient's anatomy. It is that image scan data and that graphic reference structure coordinate system that can be used for the transformation to the stereotactic coordinate system associated with the space probe or navigator. All such variations in transformations and mapping of coordinate systems and corrections with respect to patient movement or aberrations in the image scan data can be taken into account and is claimed within the scope of this patent.

It should be noted that the detection apparatus which tracks and/or determines the position of the reference frame markers for dynamic or real-time correction of the transformation between the image scan coordinate system and the stereotactic coordinate system, or corrects for patient's movement with respect to the external apparatus or space navigator system, can be separate from and different from the space navigator apparatus itself. For example, a mechanical arm could be used for the space navigator, and an optical system could be used to track the dynamic reference markers to make corrections for patient movement. On the other hand, these two elements, the apparatus to track the dynamic reference markers and the space navigator, could in fact be the same apparatus. For example, if the space navigator is an optical system or an ultrasonic system, then it could be the selfsame apparatus.

Considering that those skilled in the art may make variations that are included within the present invention, what is claimed by U.S. Letters Patent herewith are the following claims.

We claim:

1. A stereotactic localizer system for localizing positions in a patient's anatomy based on an image scan of said patient's anatomy comprising:
   a. a skin band adapted to be fixed to the patient's skin of said patient's anatomy;
   b. reference markers connected to said skin band and detectable in image scan data produced by said image scan and having image positions in an image scan coordinate system and/or said image scan data, and having physical positions with respect to stereotactic coordinate system associated with an external apparatus near said patient's anatomy, such that said image scan coordinate system can be mapped into said stereotactic coordinate system by a transformation from said image positions to said physical positions; and,
   c. further including dynamic reference structures attached to said skin band, said dynamic reference structures having a pattern which can be detected by a detection apparatus that is in a position with respect to said stereotactic coordinate system, such that changes in position of said patient's anatomy with respect to said stereotactic coordinate system can be detected by said detection apparatus and accordingly corrections in said mapping between said image scan coordinate system and said stereotactic coordinate system can be made.

2. The apparatus of claim 1 wherein said skin band comprises a head band that can be attached to the head of the patient.

3. The apparatus of claim 1 wherein said reference markers comprise radiopaque markers which can be detected in a CT scan image through said patient's anatomy.

4. The apparatus of claim 3 wherein said radiopaque markers comprise radiopaque rings having through holes such that ink dot markings can be made on said patient's skin through said through holes.

5. The apparatus of claim 1 and further comprising a graphic reference structure which can be detected as varying data in said image scan data such that individual slice images from said image scan data can be indexed with respect to said patient's anatomy such that corrections in said image scan data resulting from changes in the position of said patient's anatomy with respect to said image scan and/or said image scan coordinate system can be made.

6. The apparatus of claim 5 wherein said graphic reference structure includes diagonal elements which produce varying index data in said image scan data whereby a mapping can be made from the coordinate system of said graphic reference structure to said image scan coordinate system.

* * * * *